United States Patent [19]

Isaac et al.

[11] 4,038,386
[45] July 26, 1977

[54] DERIVATIVE OF DESGLUCOHELLEBRIN AND THERAPEUTIC USE

[75] Inventors: Otto Isaac, Bruchkobel; Klaus Posselt, Wachtberg-Villiprott; Horst Uthemann, Frankfurt, all of Germany

[73] Assignee: Deutsch Gold- und Silber-Scheideanstalt Vormals Roessler, Frankfurt, Germany

[21] Appl. No.: 564,832

[22] Filed: Apr. 3, 1975

[30] Foreign Application Priority Data

Apr. 3, 1974 Austria .................................. 2795/74

[51] Int. Cl.$^2$ .............................................. A61K 31/70
[52] U.S. Cl. .......................................... 424/182; 536/6
[58] Field of Search ..................... 260/210.5; 424/182; 536/6

[56] References Cited

U.S. PATENT DOCUMENTS

| | | | |
|---|---|---|---|
| 3,471,470 | 10/1969 | Heider et al. | 536/6 |
| 3,732,203 | 5/1973 | Stache et al. | 260/210.5 |
| 3,836,520 | 9/1974 | Stache et al. | 260/210.5 |

*Primary Examiner*—Lewis Gotts
*Assistant Examiner*—Cary Owens
*Attorney, Agent, or Firm*—Cushman, Darby & Cushman

[57] ABSTRACT

Compounds are prepared of the formula

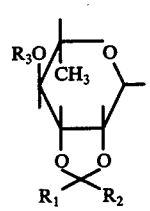

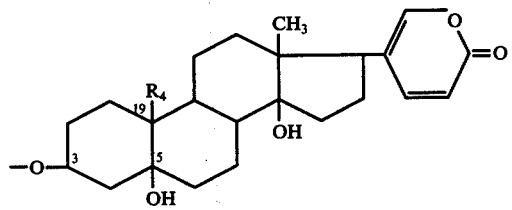

The compounds of the invention possess valuable pharmacodynamic properties. They especially have a positive inotropic effect which is particularly noted in oral or enteral application. In contrast to the known compounds the compounds of the invention have more favorable pharmacological or pharmaceutical properties.

5 Claims, 2 Drawing Figures

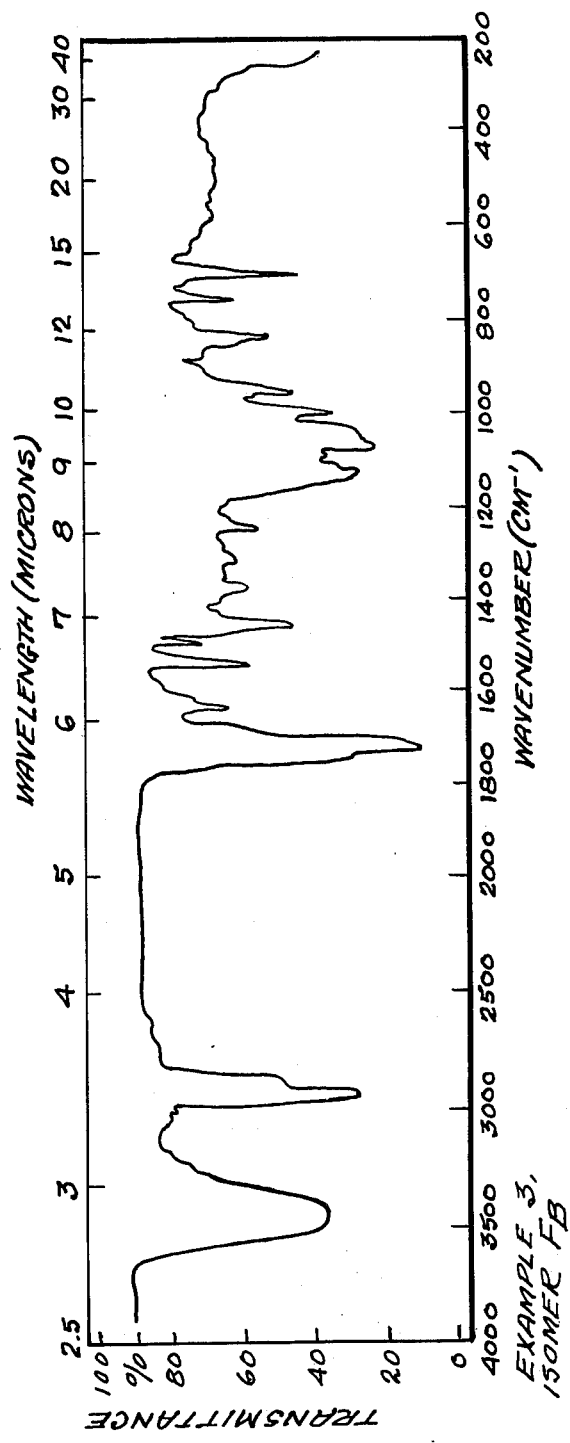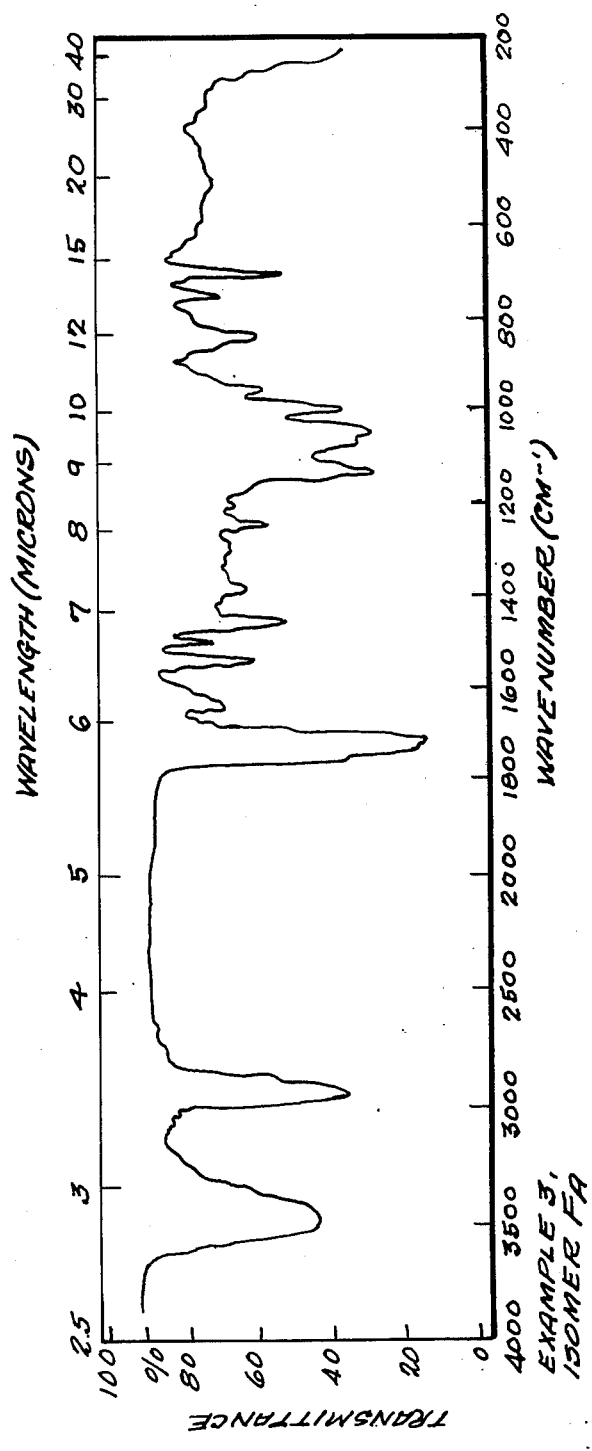

DERIVATIVE OF DESGLUCOHELLEBRIN AND THERAPEUTIC USE

The present invention relates to new derivatives of desglucohellebrin and processes for preparing them.

It is known from German Offenlegungschrift No. 1,493,274 to prepare desglucohellebrin derivatives of the formula

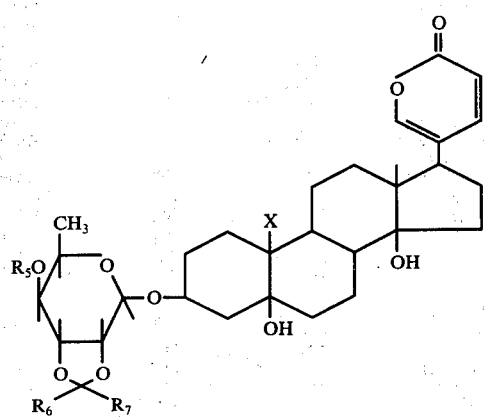

where $R_5$ is acetyl, X is formyl or hydroxymethyl and $R_2$ and $R_3$ are the same or different and are hydrogen, alkyl, chloro substituted alkyl or together with the adjacent carbon atom form a five to seven membered acyclic ring. A pharmacological activity is not set forth for these compounds. The entire disclosure of German Offenlegungsschrift No. 1,493,274 is incorporated herein by reference and relied upon.

The present invention is directed to new desglucohellebrin derivatives of the general formula I.

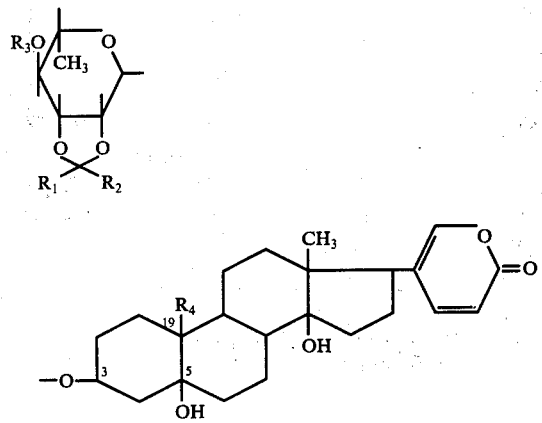

where
$R_1$ is an aliphatic acyl group having 2 to 6 carbon atoms, an alkenyl group with 2 to 8 carbon atoms, an alkinyl group with 2 to 8 carbon atoms, an alkyl group with 1 to 8 carbon atoms substituted with (1) a hydroxy group, (2) an oxo group, (3) an amino group, (4) an alkylamino group having 1 to 6 carbon atoms, (5) dialkylamino group having 1 to 6 carbon atoms in each alkyl radical, (6) an alkoxy group with 1 to 6 carbon atoms, (7) a carbalkoxy group having 1 to 6 carbon atoms in the alkoxy radical, or (8) a carboxy group, a phenyl group, benzyl group, phenylethyl group, phenyl ethenyl group, phenylethinyl group or (a) a phenyl, (b) benzyl, (c) phenyethyl, (d) phenylethenyl or (e) phenylethinyl group substituted in the benzene ring with (1) hydroxy, (2) amino, (3) monoalkylamino having 1 to 6 carbon atoms, (4) dialkylamino having 1 to 6 carbons in each alkyl group, (5) nitro, (6) alkyl of 1 to 6 carbon atoms, or (7) alkoxy with 1 to 6 carbon atoms, halogen substituted phenyl, halogen substituted benzyl, halogen substituted phenylethyl or halogen substituted phenyl, ethinyl group, $R_2$ is hydrogen, alkenyl with 2 to 8 carbon atoms, alkinyl with 2 to 8 carbon atoms, alkyl with 1 to 8 carbon atoms, alkyl with 1 to 8 carbon atoms substituted with (1) a hydroxy group, (2) an amino group, (3) an alkylamino group having 1 to 6 carbon atoms (4) a dialkylamino group having 1 to 6 carbon atoms in each alkyl group or (5) halogen, a phenyl group, benzyl group, phenylethyl group or (a) a phenyl, (b) benzyl or (c) phenylethyl group substituted in the benzene ring with (1) hydroxy, (2) amino, (3) monoalkylamino having 1 to 6 carbon atoms, (4) dialkylamino having 1 to 6 carbon atoms in each alkyl group, (5) nitro, (6) alkyl of 1 to 6 carbon atoms, (7) alkoxy with 1 to 6 carbon atoms or (8) halogen, $R_3$ is hydrogen, an aliphatic acyl group of 1 to 6 carbon atoms, benzoyl, alkyl with 1 to 6 carbon atoms, an alkoxyalkyl in which the alkoxy and alkyl groups each having 1 to 6 carbon atoms, or an alkoxycarbonyl group having 1 to 7 carbon atoms, and $R_4$ is formyl or hydroxymethyl and pharmaceutically acceptable salts thereof.

The salts should be salts with pharmaceutically acceptable acids and bases, e.g., acetic acid hydrochloric acid, propionic acid, lactic acid, citric acid, maleic acid, phosphoric, sodium hydroxide, potassium hydroxide, etc.

The compounds of the invention possess valuable pharmacodynamic properties. They especially have a positive inotropic effect which is particularly noted in oral or enteral application. In contrast to the known compounds the compounds of the invention have more favorable pharmacological or pharmaceutical properties.

The alkyl, alkenyl and alkinyl groups can be straight or branch chain. The alkyl groups in the compounds preferably have 1 to 4 carbon atoms, the alkenyl and alkinyl groups preferably 3 to 5 carbon atoms. As halogens there are employed those having an atomic weight of 9 to 80, i.e., fluorine, chlorine or bromine, preferably chlorine or bromine.

The alkoxy groups, monoalkyl and dialkylamino groups, acyl groups and carbalkoxy groups preferably have 1 to 3 carbon atoms in the alkyl group. An example of acyl is acetyl.

In compounds of formula I preferably $R_1$ is benzyl, phenethyl, phenethenyl or phenethinyl, alkenyl of 2 to 6 carbon atoms or alkinyl of 2 to 6 carbon atoms and $R_2$ is hydrogen, alkyl with 1 to 6 carbon atoms, an alkenyl group with 2 to 6 carbon atoms or an alkinyl group with 2 to 6 carbon atoms.

It is specifically preferred where $R_1$ is acyl that it be acetyl. In case the phenyl, benzyl, phenethyl, phenethenyl and phenethinyl groups are substituted in the benzene ring usually 1 to 2 substituents, preferably one substituent, are present.

In addition to the compounds set forth in the working examples other compounds within formula I and within the present invention that can be prepared in the same manner are set forth in Table I having the indicated R groups.

TABLE I

| R₁ | R₂ | R₃ | R₄ |
|---|---|---|---|
| acetyl | H | H | formyl |
| H₂NCH₂ | H | H | formyl |
| CH₃NHCH₂ | H | H | formyl |
| (CH₃)₂NCH₂ | H | H | formyl |
| HOCH₂ | H | H | formyl |
| CH₃OCH₂ | H | H | formyl |
| C₂H₅OCH₂ | H | H | formyl |
| H₂NCH₂CH₂CH₂ | H | H | formyl |
| CH₃OCH₂CH₂CH₂ | H | H | formyl |
| CH₂=C(CH₃)— | CH₃ | H | formyl |
| phenyl | H | H | formyl |
| o-ethoxyphenyl | H | H | formyl |
| 2-bromophenyl | H | H | formyl |
| 2,3-dimethoxyphenyl | H | H | formyl |
| 3,4-dimethoxyphenyl | H | H | formyl |
| 4-dimethylaminophenyl | H | H | formyl |
| 2-methoxyphenyl | H | H | formyl |
| 3-methoxyphenyl | H | H | formyl |
| 4-methoxyphenyl | H | H | formyl |
| 3-hydroxyphenyl | H | H | formyl |
| 4-hydroxyphenyl | H | H | formyl |
| 4-nitrophenyl | H | H | formyl |
| phenylethenyl | H | H | formyl |
| benzyl | CH₃ | H | formyl |
| phenyl | CH₃ | H | formyl |
| phenyl | C₂H₅ | H | formyl |
| 4-aminophenyl | C₂H₅ | H | formyl |
| 4-dimethylaminophenyl | C₂H₅ | H | formyl |
| 4-methylphenyl | C₂H₅ | H | formyl |
| 4-hydroxyphenyl | C₂H₅ | H | formyl |
| 2-hydroxyphenyl | phenyl | H | formyl |
| 4-hydroxyphenyl | phenyl | H | formyl |
| propionyl | H | H | formyl |
| butyryl | H | H | formyl |
| CH₃(CH₂)₄C(=O)— | H | H | formyl |
| vinyl | H | H | formyl |
| phenyl | vinyl | H | formyl |
| phenyl | propenyl | H | formyl |
| benzyl | propenyl | H | formyl |
| butenyl | H | H | formyl |
| benzyl | butenyl | H | formyl |
| ethinyl | H | H | formyl |
| propinyl | H | H | formyl |
| butinyl | H | H | formyl |
| 1-octenyl | H | H | formyl |
| phenyl | 1-octenyl | H | formyl |
| pentenyl | H | H | formyl |
| benzyl | pentenyl | H | formyl |
| pentinyl | H | H | formyl |
| propenyl | CH₃ | H | formyl |
| H₂N(CH₂)₄ | H | H | formyl |
| aminoethyl | H | H | formyl |
| diethylaminobutyl | H | H | formyl |
| dibutylaminomethyl | H | H | formyl |
| butylaminomethyl | H | H | formyl |
| aminohexyl | H | H | formyl |
| dimethylaminohexyl | H | H | formyl |
| methoxymethyl | H | H | formyl |
| butoxyethyl | H | H | formyl |
| hexoxyethyl | H | H | formyl |
| methoxybutyl | H | H | formyl |
| ethoxyhexyl | H | H | formyl |
| carbomethoxyethyl | H | H | formyl |

TABLE I-continued

| R₁ | R₂ | R₃ | R₄ |
|---|---|---|---|
| carboethoxymethyl | H | H | formyl |
| carbobutoxyethyl | H | H | formyl |
| carboethoxybutyl | H | H | formyl |
| carbohexoxymethyl | H | H | formyl |
| carboxymethyl | H | H | formyl |
| carboxyethyl | H | H | formyl |
| carboxybutyl | H | H | formyl |
| carboxyoctyl | H | H | formyl |
| phenethenyl | CH₃ | H | formyl |
| phenethenyl | phenyl | H | formyl |
| phenethinyl | H | H | formyl |
| phenyl | CH₃ | H | formyl |
| phenyl | ethyl | H | formyl |
| phenyl | butyl | H | formyl |
| phenyl | octyl | H | formyl |
| phenyl | 4-chlorophenyl | H | formyl |
| 2-fluorophenyl | methyl | H | formyl |
| 4-chlorophenyl | 4-chlorophenyl | H | formyl |
| 3-bromophenyl | butyl | H | formyl |
| 4-butoxyphenyl | H | H | formyl |
| 4-butoxyphenyl | benzyl | H | formyl |
| phenethyl | H | H | formyl |
| phenethyl | methyl | H | formyl |
| phenethyl | phenethyl | H | formyl |
| 2-methyl-4-chlorophenyl | H | H | formyl |
| 2-methyl-4-chlorophenyl | phenyl | H | formyl |
| 3-nitrophenyl | phenyl | H | formyl |
| 4-nitrophenyl | 4-nitrophenyl | H | formyl |
| 4-hexylphenyl | H | H | formyl |
| C₂H₅OC₂H₅ | H | CH₃C(=O) | formyl |
| benzyl | ethyl | propionyl | formyl |
| benzyl | methyl | butyryl | formyl |
| phenyl | H | acetyl | formyl |
| phenyl | propyl | acetyl | formyl |
| phenyl | methyl | formyl | formyl |
| benzyl | ethyl | benzoyl | formyl |
| phenyl | H | benzoyl | formyl |
| methoxypropyl | H | methyl | formyl |
| benzyl | ethyl | ethyl | formyl |
| phenyl | H | butyl | formyl |
| phenyl | methyl | hexyl | formyl |
| phenyl | H | methoxyethyl | formyl |
| CH₃CH=CH | H | H | hydroxymethyl |
| C₂H₅OC₂H₅— | H | H | hydroxymethyl |
| benzyl | ethyl | H | hydroxymethyl |
| benzyl | ethyl | acetyl | hydroxymethyl |
| methoxypropyl | H | H | hydroxymethyl |
| CH₃CCH₂—(=O) | H | H | hydroxymethyl |
| benzyl | ethyl | butyryl | hydroxymethyl |
| benzyl | benzyl | H | hydroxymethyl |
| phenyl | phenyl | H | hydroxymethyl |

The production of the compounds of the invention can take place by reacting a compound of the formula II

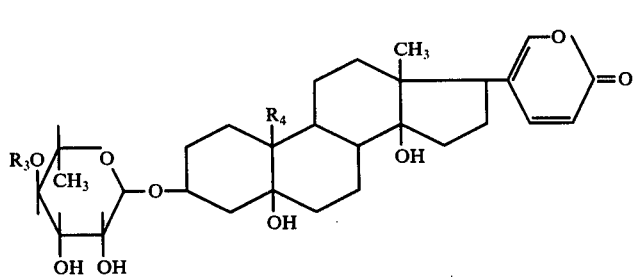

II where R₃ and R₄ are as defined above with a compound of formula III

where $R_1$ and $R_2$ are as defined above and Z is an oxygen atom of two lower alkoxy groups, and, in a given case reacting the compound obtained with a compound of the formula Y—$R_3$ wherein $R_3$ is as defined above and Y is chlorine, bromine or iodine, benzoyloxy, a lower aliphatic acyloxy (e.g., alkanoyloxy with 1 to 6 carbon atoms such as formyloxy, acetyloxy, propionyloxy, butyryloxy, hexanoyloxy), a phenylsulfonyloxy group, an alkylphenylsulfonyloxy group (e.g., p-toluenesulfonyloxy) or the group —O(SO$_2$)$_{1/2}$ in a solvent, in a given case in the presence of an acid binding agent, e.g., a base such as pyridine, dibutylamine, dimethylaniline, aniline, etc., and/or reducing a formyl group present in the 19-position to a hydroxymethyl group.

The compounds obtained can be converted into their salts, e.g., with nontoxic acids and bases as pointed out supra.

Examples of compounds within formula III are pyruvic aldehyde dimethyl acetal, aminoacetaldehyde diethyl acetal, methylaminoacetaldehyde dimethyl acetal, dimethylaminoacetaldehyde diethyl acetal, 2-hydroxyacetaldehyde diethyl acetal, methoxyacetaldehyde diethyl acetal, 3-ethoxypropionaldehyde diethyl acetal, 4-aminobutyraldehyde dimethyl acetal, crotonaldehyde diethyl acetal, methyl isopropenyl ketone diethyl ketal, benzaldehyde diethyl acetal, 4-ethoxybenzaldehyde diethyl acetal, 2-bromobenzaldehyde diethyl acetal, 2,3-dimethoxybenzaldehyde diethyl acetal, 3,4-dimethoxybenzaldehyde diethyl acetal, 4-dimethylaminobenzaldehyde diethyl acetal, 2-methoxybenzaldehyde diethyl acetal, 3-methoxybenzaldehyde diethyl acetal, 4-methylbenzaldehyde diethyl acetal, 3-hydroxybenzaldehyde diethyl acetal, 4-hydroxybenzaldehyde diethyl acetal, 4-nitrobenzaldehyde diethyl acetal, cinnamic aldehyde diethyl acetal, benzyl methyl ketone diethyl ketal, ethyl benzyl ketone diethyl ketal, acetophenone diethyl ketal, propiophenone diethyl ketal, 4'-aminopropiophenone diethyl ketal, 4'-dimethylaminopropiophenone diethyl ketal, 4'-methyl propiophenone diethyl ketal, 4'-hydroxypropiophenone diethyl ketal, benzophenone diethyl ketal, 2-hydroxybenzophenone diethyl ketal, 4-hydroxybenzophenone diethyl ketal.

The compound of formula III for example can be added in excess. It is convenient to carry out the reaction in the presence of an acid catalyst or condensation agent. As such acid catalysts there can be used for example mineral acids in low concentration, sulfonic acids or water free Lewis acids as for example hydrochloric acid, sulfuric acid, phosphoric acid, methane sulfonic acid, p-toluenesulfonic acid, benzenesulfonic acid, boron trifluoride etherate, iron (III) chloride, zinc chloride, water free (anhydrous) copper sulfate or cation exchanges in the acid form, e.g., sulfonated styrene-divinyl benzene copolymer. As cation exchangers there are H+ preferably used organic ion exchangers. After conversion into the H+ by treatment with an inorganic strong acid, e.g., sulfuric acid or hydrochloric acid, the ion exchangers are washed water free with organic solvents and dried. After the end of the reaction the reaction mixture is filtered off with suction from the solid ion exchange resin. In this way there is avoided an additional neutralization of the reaction mixture which under certain circumstances can lead to uncontrollable side reactions.

The reaction is generally carried out in solvents inert under the reaction conditions, as for example a lower aliphatic alcohol, e.g., alkanols such as methyl alcohol, ethyl alcohol, isopropyl alcohol, propyl alcohol, butyl alcohol and hexyl alcohol, halohydrocarbons, e.g., chloroform and carbon tetrachloride. The excess compound of formula III can likewise be used as the solvent.

Frequently it is advantageous to add the foundation ketone or aldehyde of the compound of formula III in case a compound of formula III is added in which Z is two alkoxy groups.

The process can be carried out at temperatures between 0° C. and the boiling point of the solvent. Generally temperatures between 15° and 90° C., preferably between 40° and 75° C. are employed.

To avoid the hydrolytic splitting between hellebrin and the sugar radical the reaction should be carried out in substantially water free medium.

The progress of the reaction is best followed based on thin layer chromatographic analysis. The working up of the reaction mixture then is carried out when no or only a little desglucohellebrin is detected.

With sensitive, easily oxidizable ketals or acetals the process is preferably carried out in an inert gas atmosphere, for example under nitrogen.

After the end of the reaction the condensation is neutralized and the excess compound of formula III either distilled off or the reaction product precipitated, (for example by means of ether, petroleum ether, gasoline or water). The reaction product can be purified subsequently, for example by chromatograhy or silica gel.

In case the groups $R_1$ and $R_2$ are different two isomeric compounds are possible in which the groups $R_1$ and $R_2$ are exchanged with each other in regard to their spatial position. In a given case both isomeric compounds are produced simultaneously so that the final product is a mixture of both isomers. If desired such a mixture can be separated in the customary manner. For example the separation of the isomers can be carried out by thin layer chromatography on silica gel final plate with indicator whereby the mixture of substances is dissolved in a suitable solvent and in distributed in bands on the silica gel. As solvents to bring the materials out on the silica gel plate there can be used for example lower aliphatic alcohols, e.g., methyl alcohol, ethyl alcohol, butyl alcohol and isopropyl alcohol, lower halohydrocarbons with 1 to 4 halogen atoms, especially chlorine atoms, e.g., chloroform, methylene chloride and carbon tetrachloride, cyclic ethers, e.g., dioxane and tetrahydrofuran, esters of lower aliphatic carboxylic acids with lower aliphatic acids, e.g., methyl acetate, ethyl acetate, butyl acetate, methyl propionate and methyl butyrate, amides of lower aliphatic carboxylic acids and carbonic acid which in a given case are substituted on the nitrogen atom by lower alkyl groups, for example methyl groups, e.g., dimethyl formamide and dimethyl acetamide, as well as mixtures of these agents. As flow agents there can be used for example mixtures of lower halohydrocarbons and lower aliphatic alcohols as for example carbon tetrachloride-n-butanol in the ratio 60–95 : 5–40 (by volume), preferably 80:20 or esters of lower carboxylic acids and lower aliphatic alcohols as for example ethyl acetate-methanol in the ratio 80–99 : 1–20 (by volume), preferably 98:2.

The separated zones were traced in ultra-violet light and cleaned off of the plate. The separated substance can be extracted, for example with the help of the above-mentioned solvents. For example there can be used a mixture of chloroform and methanol, preferably in the ratio 1:1 (by volume). The extracts are concentrated to dryness and the residue dissolved in a suitable solvent (as those given above or also an aromatic hydrocarbon such as benzene or an aromatic hydrocarbon substituted with halogen or methyl, e.g., chlorobenzene or toluene) and precipitated (for examples with petroleum ether).

By reaction with compounds of the formula Y—$R_3$, in a given case the group $R_3$ is introduced. Among these compounds there are used for example acyl halides or acid anhydrides, as for example acid anhydrides of lower aliphatic acids with 1 to 6 carbon atoms, e.g., acetic anhydride, propionic anhydride, butyric anhydride, valeric anhydride and caproic anhydride, acid bromides or chlorides of aliphatic fatty acids with 1 to 6 carbon atoms, e.g., acetyl chloride, acetyl bromide, phosgene, propionyl bromide, propionyl chloride, butyryl chloride, caproyl chloride and caproyl bromide, benzoic anhydride, benzoyl halides, e.g., benzoyl chloride, benzoyl bromide, aliphatic ketenes with 2 to 6 carbon atoms, e.g., ketene, methyl ketene, ethyl ketene, dimethyl ketene and diethyl ketone, mixed anhydrides of aliphatic carboxylic acids with 1 to 6 carbon atoms and a carbonic acid monoester with 1 to 6 carbon atoms, e.g. acetyl monoethyl carbonate, alkyl halides with 1 to 6 carbon atoms, e.g., methyl chloride, methyl bromide, methyl iodide, ethyl chloride, ethyl bromide, ethyl iodide, propyl chloride, propyl bromide, isopropyl chloride, butyl bromide, sec. butyl chloride, amyl chloride, amyl bromide, hexyl chloride, hexyl bromide, alkoxy substituted alkyl halides having 1 to 6 carbon atoms in the alkoxy and the alkyl groups, e.g., methoxyethyl chloride, ethoxymethyl bromide, hexoxyethyl chloride, methoxyhexyl chloride, butyoxypropyl chloride, methoxybutyl chloride or dialkyl sulfates having alkyl groups of 1 to 6 carbon atoms, e.g., dimethyl sulfate, diethyl sulfate, dipropyl sulfate, dibutyl sulfate and dihexyl sulfate. This reaction is carried out in a solvent or suspension agent (for example alcohols, e.g., methyl alcohol, ethyl alcohol and butyl alcohol, dioxane, dimethyl formamide, dimethyl sulfoxide, acetone and aromatic hydrocarbons such as benzene or toluene), for example at temperatures between 20° and 120° C. In a given case it is favorable to have an acid binding agent present. As acid binding agents there can be used for example inorganic bases and tertiary organic bases such as barium oxide, barium hydroxide, silver oxide, dimethyl aniline and pyridine. In a given case the organic base can also be used simultaneously as the solvent.

The reduction of the formyl group ($R_4$) of the derivative of the desglucohellebrin to the corresponding methylol compound can be carried out in known manner with metal hydrides or complex metal hydrides such as sodium hydride, sodium borohydride or lithium tri-tert. butoxy aluminum hydride in a solvent. Preferably for example the reduction with sodium borohydride can be carried out in a water miscible solvent such as dioxane or tetrahydrofurane. As temperature range for the reduction there can be used, for example, 0° to 70° C., preferably 0° to 25° C.

Favorable effects are shown for example by compounds wherein $R_3$ and $R_4$ have the definitions set forth above and $R_1$ and $R_2$ are the same or different and are hydrogen, alkyl groups with 1 to 6 carbon atoms, especially 1 to 4 carbon atoms, alkenyl groups with 2 to 8, especially 2 to 6 carbon atoms, alkinyl groups with 2 to 6 carbon atoms, especially 3 to 4 carbon atoms, the benzyl group, phenethyl group, phenyl ethenyl group or phenyl ethinyl group. (Excluded are compounds wherein $R_1$ and $R_2$ are both hydrogen or both alkyl groups or one of $R_1$ and $R_2$ is hydrogen and the other is alkyl).

In the drawings

FIG. 1 is the IR spectrum of compound $F_B$ prepared in Example 3, and

FIG. 2 is the IR spectrum of compound $F_A$ prepared in Example 3.

Unless otherwise indicated, all parts and percentages are by weight.

EXAMPLE 1

3β-(2′,3′-Buten-(2)-yliden-(1)-α-L-rhamnosido)-5β,14β-dihydroxy-19-oxo-bufa-20,22-dienolide 3 grams of desglucohellibrin were heated in 40 ml of dioxane and 20 ml of chloroform with 10 ml of crotonaldehyde diethyl acetate in the presence of 0.1 gram of p-toluenesulfonic acid for 2 hours with stirring at 50° to 55° C. Then there were added 0.2 ml of pyridine, the solvent distilled off in a vacuum and the residue treated with isopropyl ether. These were obtained 3 grams of crude product which was chromatographed over a silica gel column. Elution with chloroform-methanol-water (1950:45:5 by volume) yielded 1.8 grams of homogeneous title compound which was recrystallized from 120 ml of 90% ethanol. Yield 0.5 grams, M.P. 236° to 237° C.

EXAMPLE 2

3β-{2′,3′-[n-(3-Ethoxy)-propyliden-(1)]-α-L-rhamnosido}-5β,14β-dihydroxy-19-oxo-bufa-20,22-dienolide 2.8 grams of desglucohellebrin were heated at 55° to 60° C. with stirring in 150 ml of dioxane with 25 grams of 3-ethoxypropionaldehyde diethyl acetal and 0.1 grams of p-toluenesulfonic acid for 4 hours. There were then added 0.2 ml of pyridine, the solvent distilled off under a vacuum, and the concentrate chromatographed on a silica gel column (silica gel M, Gebr. Herrmann, Cologne-Ehrenfeld). It was eluted with chloroform-methanol (98:2 by volume). There were obtained 450 mg of the title compound which was dissolved in benzene and precipitated from petroleum ether. Yield 410 mg; M.P. 131° C.

EXAMPLE 3

3β-{2′,3′-[1-Phenylbutyliden-(2)]-α-L-rhamnosido}-5β,14β-dihydroxy-19-oxobufa-20,22-dienolide 60 grams of desglucohellebrin were heated at 55° C for 4 hours with stirring in 1.5 liters of dioxane with 200 ml of ethyl benzyl ketone diethyl ketal and 100 ml of ethyl benzyl ketone in the presence of 2 grams of p-toluenesulfonic acid. Then 4 ml of pyridine were added and the solvent distilled off in a vacuum. The crude product was precipitated from the concentrate with a maximum of 10 liters of petroleum ether. There were obtained 100 grams of crude product which was chromatographed on a silica gel column (2 kg silica gel M, Gebr. Herrmann, Cologne-Ehrenfeld.) The elution from the silica gel was carried out with chloroform-methanol (99:1 by volume).

There were obtained about 57 grams of product which was dissolved in 250 ml of benzene and precipitated with 3 liters of petroleum ether. The product (37 grams) thus obtained having a melting point of 143° to 145° C., was a mixture of two isomers which differed from each other in that the groups $R_1$ and $R_2$ were exchanged with each other. This mixture can be separated into the two pure compounds for example by the following procedure.

Separation of the Isomers From the Mixture Obtained According to Example 3

Employing the Autoliner (Desaga) there were incorporated on the final plate for thin layer chromatography (Merck, silica gel F-254, layer thickness 0.5 mm, size 20 × 20 cm) each time 20 mg of the isomeric mixture dissolved in 2 ml of chloroform-methanol (95:5 by volume) per plate.

As flow agent there was employed carbon tetrahchloride-n-butanol in the ratio 80:20 (by volume). The separated zones were traced in ultra-violet light and then cleaned off of the plate. The compounds were extracted from the silica gel with chloroform-methanol (50:50 by volume). After the concentration of the extracts to dryness, the residues were dissolved in a little hot benzene and compounds A and B were precipitated with petroleum ether, filtered with suction and dried.

One isomer ($F_A$) melts at 143°-145° C and the other isomer ($F_B$) at 139° C.

UV-absorption: Both isomers have a maximum at 300 nm (in methanol).

IR absorption: There are aromatic bands at 3050, 3030, 745, and 695 cm$^{-1}$, aldehyde carbonyl bands at 1710 cm$^{-1}$ and lactone carbonyl bands at 1740 cm$^{-1}$, C=C, double bond bands at 1618 cm$^{-1}$. A difference is shown between the two isomers only in the fine structure in the region between 1030 cm$^{-1}$ and 1340 cm$^{-1}$ as is shown by the spectra depicted in FIG. 1 of the drawings for isomer $F_B$ and in FIG. 2 for isomer $F_A$.

EXAMPLE 4

3β-{4'-Acetyl-2',3'-[1-Phenylbutyliden-(2)]-α-L-rhamnosido}-5β,14β-dihydroxy-19-oxo-bufa-20,22-dienolide 6.9 grams of 3β-{2'3'-[1-Phenylbutyliden-(2)]-α-L-rhamnosido}-5β, 14β-dihydroxy-19-oxo-5 -bufa-20,22-dienolide were dissolved in 30 ml of pyridine and the solution treated with 20 ml of acetic anhydride. After standing overnight at room temperature the crude product was precipitated with 50 ml of water. The crude product was chromatographed on a silica gel column (silica gel M, Gebr. Herrmann, Cologne-Ehrenfeld). The elution of the title compound was successful with chloroform methanol (99:1 by volume).

The compound was dissolved in benzene and precipitated with petroleum ether.

Yield: 1.4 grams; M.P. 132° to 135° C.

EXAMPLE 5

3β-{2',3'-[n-(3-Methoxy)-butyliden-(1)]-α-L-rhamnosido}-5β,14β-dihydroxy-19-oxo-bufa-20,22-dienolide 2.8 grams of desglucohellebrin were heated with stirring at 55° C. for 4 hours in 150 ml of dioxane with 25 ml of 3-methoxybutyraldehyde dimethyl acetal in the presence of 0.1 gram of p-toluene-sulfonic acid. Then there were added 0.2 ml of pyridine and the solvent distilled off under a vacuum. The crude product was precipitated from the concentrate with petroleum ether and chromatographed twice on a silica gel column (silica gel M, Gebr. Hermann, Cologne-Ehrenfeld). The elution took place with chloroform-methanol (85:15 by volume). The title compound thus precipitated was dissolved in benzene and precipitated with petroleum ether.

Yield: 400 mg; M.P. 138° to 140° C.

EXAMPLE 6

3β-{2',3'-[2-Acetoethyliden-(1)]-α-1-rhamnosido}-5β,14β-dihydroxy-19-oxo-bufa-20,22-dienolide 2.8 grams of desglucohellebrin were heated at 55° C. with stirring for 4 hours in 150 ml of dioxane with 20 ml of acetoacetaldehyde dimethyl acetate in the presence of 200 mg of p-toluenesulfonic acid.

0.4 ml of pyridine was there added and the solvent distilled off under vacuum. The concentrate was dissolved in a little chloroform and chromatographed twice on a silica gel column (silica gel M, Gebr. Herrmann, Cologne-Ehrenfeld). The title compound was eluted with chloroform-methanol (95:5 by volume). The compound was dissolved in hot benzene and precipitated with petroleum ether.

Yield: 515 mg; M.P. 145° to 148° C.

EXAMPLE 7

3β-{4'-Butyryloxy-2',3'-[1-Phenylbutyliden(2)]-α-rhamnosido}-5,14-dihydroxy-19-oxo-5β-bufa-20,22-dienolide 2.31 grams (0.0033 Mol) of 3β-{2',3'-[1-Phenylbutyliden-(2)]-rhamnosido}-5,14-dihydroxy-19-oxo-5β-bufa-20,22-dienolide were stirred for 1 hour at room temperature in 20 ml of pyridine with 10 ml of butyric anhydride and then boiled for 1 hour at reflux. The reaction solution was concentrated under a vacuum and chromatrographed twice on silica gel. It was eluted with chloroform-methanol (98:2 by volume). The fractions cleansed by the chromatography and then eluted were combined and concentrated to dryness under a vacuum. The title compound obtained was dissolved in chloroform and precipitated with petroleum ether.

Yield: 0.2 gram, N.P. 119° C.

EXAMPLE 8

3β-[2',3'-(1,3-Diphenylisopropyliden)-α-L-rhamnosido]-5,14-dihydroxy-19-oxo-5β-bufa-20,22-dienolide 2.8 grams of desglucohellebrin were suspended in 75 ml of dioxane and after the addition of 15 ml of dibenzyl ketone diethyl ketal and 100 mg of p-toluenesulfonic acid stirred for 4 hours at 60° C. Then there were added 0.2 ml of pyridine and the mixture concentrated under a vacuum and chromatographed twice on a silica gel column. Elution was carried out with chloroform-methanol (95:5 by volume).

The combined fractions were concentrated to dryness under vacuum, the residue dissolved in a little hot benzene and precipitated with petroleum ether.

Yield: 0.3 gram; M.P. 141°-142° C.

EXAMPLE 9

3β-[2',3'-(Diphenylformyliden)-α-L-rhamnosido]-5,14-dihydroxy-19-oxo-5β-bufa-20,22-dienolide 2.8 grams (0.005 mole) of desglucohellebrin, 15 grams of benzophenone diethyl ketal and 0.1 gram of p-toluenesulfonic acid were stirred in 75 ml of dioxane for 6 hours at 60° C. The course of the reaction was followed by thin layer chromatography. After the ending of the reaction there were added 0.2 ml pyridine, the solution concentrated under a vacuum and the crude product precipitated with ether. The purification took place through a two-fold chromatography on silica gel columns with chloroform-methanol (98:2 by volume) as the running medium. The clean fractions were united and concentrated to dryness. The residue was dissolved in benzene and the title compound precipitated with petroleum ether.

Yield: 0.5 gram; M.P. 172°-174° C.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place in known manner with the use of known and customary pharmaceutical assistants as well as other customary carriers and diluents.

Such carriers and assistants are set forth for example in Ullmann's Encyklopaedie der technischer Chemie, Vol. 4 (1953), pages 1 to 39; Journal of Pharmaceutical Sciences, Vol. 52 (1963), pages 918 et seq.; H. v. Czetsch-Lindenwald, Hilfstoffe fuer Pharmazie und angrensende Gebiete; as well as in Pharm. Ind. Vol. 2 (1961), pages 72 et seq.; Dr. H. P. Fieldler, Lexicon der Hilfstoffe fuer Pharmazie, Kosmetik and angrenzende Gebiete, Cantor Kg. Aulendorf i. Wurtt, 1971.

Examples of such materials include gelatin, natural sugars such as sucrose and lactose, lecithin, pectin, starch (for example corn starch), alginic acid, Tylose (methyl cellulose), talc, lycopodium, silica (for example colloidal silica), cellulose (e.g. micropulverized cellulose), cellulose derivatives (for example cellulose ethers in which the cellulose hydroxy groups are partially etherified with lower saturated aliphatic alcohols and-/or lower saturated aliphatic hydroxy alcohols, for example methyl cellulose, ethyl cellulose, methyl hydroxypropyl cellulose, hydroxyethyl cellulose and carboxymethyl cellulose), stearates, e.g., methyl stearate and glyceryl stearate, magnesium and calcium salts of fatty acids with 12 to 22 carbon atoms, especially saturated fatty acid salts such as calcium stearate and magnesium stearate as well as calcium laurate, magnesium laurate, calcium palmitate, magnesium palmitate, calcium oleate and magnesium oleate, calcium behenate and magensium behenate, emulsifiers, oils and fats, especially vegetable oils (for example peanut oil, castor oil, olive oil, sesame oil, cottonseed oil, corn oil, wheat germ oil, sunflower seed oil, codliver oil, mno, di and triglycerides of saturated fatty acids of $C_{12}H_{24}O_2$ to $C_{18}H_{36}O_2$ and their mixtures, e.g., glyceryl tristearate, glyceryl monostearate, glyceryl distearate, glyceryl trilaurate, glyceryl tripalmitate and glyceryl dilaurate, pharmaceutically compatible mono and polyhydric alcohols and polyglycols such as polyethylene glycols and their derivatives such as glycerine, mannitol, sorbitol, pentaerythritol, ethyl alcohol, diethylene glycol, triethylene glycol, ethylene glycol, propylene glycol, dipropylene glycol, polyethylene glycol 400, esters of aliphatic saturated and unsaturated fatty acids (2 to 22 carbon atoms, especially 10 to 18 carbon atoms) with monovalent aliphatic alcohols (1 to 20 carbon atoms) or polyhydric alcohols such as glycols, glycerine, diethylene glycol, pentaerythritol, sorbitol, mannitol, etc., which in a given case can be etherified, e.g., glyceryl tristearate, glyceryl tripalmitate, glyceryl trioleate, glyceryl triacetate, glyceryl diacetate, glyceryl monoacetate, glyceryl tricaprylate, glyceryl monocapyrlate, ethylene glycol distearate, ethylene glycol monostearate, ethyl stearate, ethyl capyrlate, ethyl behenate, benzyl benzoate, dioxolane, glycerine formal, glycol furfural, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, for example, ethanol, 1,2-propylene glycol, polyglycols, e.g., diethylene glycol and tetraethyleneglycol, and their derivatives, dimethyl sulfoxide, fatty alcohols, triglycerides, partial esters of glycerine, paraffin and the like.

In the production of the preparations there can be used the known and conventional solvent aids and emulsifiers there can be used for example polyvinyl pyrrolidone, sorbitan fatty acids such as sorbitan trioleate, lecithin, gum acacia, gum tragacanth, polyoxyethylated sorbitan monooleate, polyoxyethylated fats, polyoxyethylated oleotriglycerides, linolenized oleotriglycerides, polyethylene oxide condensation products of fatty alcohols, alkylphenols and fatty acids. By polyoxyethylated is meant that the materials concerned contain polyoxyethylene chains whose degree of polymerization is generally between 2 and 40 and especially between 10 and 20.

Such polyoxyethylated materials can be obtained for example by reaction of hydroxyl group containing compounds (for example mono or diglycerides or unsaturated compounds as for example those which contain oleic acid groups reacted with ethylene oxide (for example 40 moles of ethylene oxide per mole of glyceride).

Examples of oleotriglycerides are olive oil, peanut oil, castor oil, sesame oil, cottonseed oil, corn oil (also see Dr. H. P. Fiedler, Lexikon der Hilfstoffe fuer Pharmazie, Kosmetik und angrenzende Gebiete (1971) pages 191 to 195).

Furthermore there can be added preservatives, stabilizers, buffers, for example, calcium hydrogen phosphate and sodium hydrogen phosphate, colloidal aluminum hydroxide, taste correctives, antioxidants and complex formers (for example ethylenediamine tetraacetic acid) and the like. In a given case for stabilization of the active molecule the pH can be regulated to about 3 to 7 with physiologically compatible acids or buffers. Generally it is preferred to have a pH which ranges from as close to neutral as possible to weakly acid (to pH 5).

As antioxidants there can be used, for example, sodium meta bisulfite, ascorbic acid, gallic acid, gallic acid alkyl esters, e.g., methyl gallate, butyl hydroxy anisole (BHT), nordihydroquaiaretic acid, tocopherol as well as tocopherol plus synergists (materials which complex heavy metals by binding as complexes, for example lecithın, ascorbic acid, phosphoric acid). The addition of synergists considerably increases the antioxidant activity of tocopherol. As preservatives there can be used for example, sorbic acid, p-hydroxybenzoic acid esters (for example lower alkyl esters such as methyl p-hydroxybenzoate and ethyl p-hydroxybenzoate), benzoic acid, sodium benzoate, trichloroisobutyl alcohol, phenol, cresol, benzethonium chloride and formalin derivatives.

The pharmacological and galenic handling of the compounds of the invention takes place according to customary standard methods. For example the active material (or materials) and assistants or carriers are well mixed by stirring or homogenization (for example by means of colloid mills or ball mills), whereby generally temperatures between 20° and 80° C., preferably 20° to 50° C. are employed.

The medicines can be used for example orally, parenterally, perlingually or rectally.

It is also possible to add other medicines.

The compounds of the invention have a good positive inotropic effect on the papillary muscle (in guinea pigs) and in the entire animal (in dogs).

This activity is comparable to the known medicine β-methyl digoxin.

The lowest safe effective dosage in the above-mentioned animal experiments for example is 0.15 mg/kg orally
0.15 mg/kg intravenously.

As a general range of dosage for activity (animal experiments as above) there can be used for example 0.1–0.3 mg/kg orally
0.1–0.3 mg/kg intravenously.

The compounds of the invention find use in all forms of heart insufficiency. Thus they can be used anywhere where β-methyl digoxin is used and can also be used in place of digitalis.

The compounds can be dispensed in the form of tablets, capsules, pills, dragees, suppositories, or in liquid form. As liquids there can be used oily alcoholic, or aqueous solutions or suspensions and emulsions. The preferred forms of use are tablets which contain between 0.05 and 0.5 mg of active material or as solutions which contain between 0.001 and 0.05% of active material.

In individual doses the amount of active component of the invention can be used, for example, (a) in an amount of 0.05 to 0.5 mg dispensed orally; (b) 0.05 to 0.5 mg dispensed intravenously or intramuscularly; 0.05 to 0.5 mg dispensed rectally.

For example, there is recommended the use of 1 tablet containing 0.05 to 0.5 mg of active ingredient 2 times daily or intravenously the invention 1 to 2 times a day of a 1 to 2 ml ampoule having 0.05 to 0.5 mg of active material.

The acute toxicity of the compounds of the invention in the mouse (expressed by the LD 50 mg/kg method of Miller and Tainter, Proc. Soc. Exer. Biol. and Med., Vol. 57 (1944) pages 261 et seq.) in oral application is between 1 and 2000 mg/kg.

The drugs can be used in human medicine alone or an admixture with other pharmacologically active materials. They can also be used in veterinary medicine, e.g., to treat dogs, guinea pigs, cats, etc.

The process of the invention can comprise, consist essentially of or consist of the steps set forth and the composition can comprise, consist essentially of or consist of the materials set forth.

By hydrolysis under strongly acid conditions the compounds of the invention can be broken down to form the sugar rhamnose.

What is claimed is:

1. A compound having the formula:

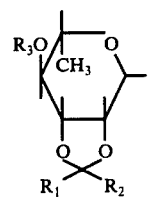

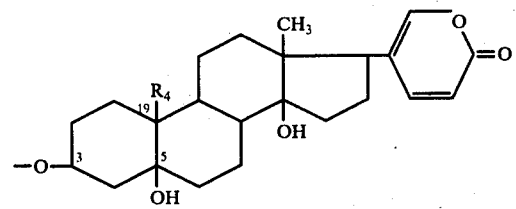

wherein one of $R_1$ and $R_2$ is benzyl and the other of $R_1$ and $R_2$ is ethyl, $R_3$ is hydrogen and $R_4$ is formyl and pharmaceutically acceptable salts thereof.

2. A process of administering to a mammal a compound according to claim 1 in an amount sufficient to have a positive inotropic effect.

3. A process according to claim 2 comprising administering the compound orally.

4. A process according to claim 2 comprising administering the compound parenterally.

5. A process according to claim 2 comprising administering the compound rectally.

* * * * *